United States Patent [19]

Nowak et al.

[11] Patent Number: 6,051,390
[45] Date of Patent: Apr. 18, 2000

[54] COMPLEX-BOUND INHIBITORS OF METABOLIC ENZYMES CAPABLE OF BEING ACTIVATED, USEFUL AS MOLECULAR MARKERS FOR DIAGNOSTIC AND THERAPY MONITORING PURPOSES

[75] Inventors: Götz Nowak; Elke Bucha, both of Erfurt; Verena Baldinger, Hammersbach, all of Germany

[73] Assignee: Max-Planck-Gesellschaft zur Förderung der Wissenschaften E.V., Berlin, Munich, Germany

[21] Appl. No.: 09/029,867

[22] PCT Filed: Aug. 1, 1996

[86] PCT No.: PCT/EP96/03383

§ 371 Date: May 26, 1998

§ 102(e) Date: May 26, 1998

[87] PCT Pub. No.: WO97/10509

PCT Pub. Date: Mar. 20, 1997

[30] Foreign Application Priority Data

Sep. 13, 1995 [DE] Germany ............ 195 33 817

[51] Int. Cl.⁷ ............... C12Q 1/56; C12Q 1/37
[52] U.S. Cl. ............... 435/13; 435/23; 435/24; 930/250
[58] Field of Search ............... 435/13, 23, 24; 530/350, 402; 514/21; 930/250

[56] References Cited

U.S. PATENT DOCUMENTS

| | | | |
|---|---|---|---|
| 4,226,775 | 10/1980 | McEvoy et al. | 260/326.33 |
| 4,853,220 | 8/1989 | Clemmensen et al. | 424/101 |
| 5,192,689 | 3/1993 | Hemker et al. | 436/69 |
| 5,362,858 | 11/1994 | Bischoff | 530/410 |
| 5,538,946 | 7/1996 | Crause et al. | 514/12 |
| 5,663,141 | 9/1997 | Kurfuerst et al. | 514/12 |

FOREIGN PATENT DOCUMENTS

| | | | |
|---|---|---|---|
| 0 345 616 | 12/1989 | European Pat. Off. | C07K 17/10 |
| 0 557 199 | 8/1993 | European Pat. Off. | C07K 17/10 |
| 92/05749 | 4/1992 | WIPO | A61F 2/00 |

OTHER PUBLICATIONS

Mast et al. Polyethylene glycol modification of serpins improves therapeutic potential. Biol. Chem. Hoppe–Seyler. vol. 371 (suppl.), pp. 101–109. (May 1990).

Patent Abstracts of Japan, vol. 012, No. 496 (C–555), Dec. 23, 1988 & JP 63 209587 (Fuji Oil Co Ltd), Aug. 31, 1988.

Database WPI, Section Ch, Week 7630, Derwent Publications Ltd., London, GB; Class B04, AN 76–57141X, XP002022851 & JP 51 020 597 B (Green Cross Corp), Jun. 26, 1976.

Webster's Collegiate Dictionary, 10th edition, p. 12. Merriam–Webster Inc., Massachusetts, USA, (1996).

Nowak et al., Quantitative determination of hirudin in blood and body fluids. Seminars in Thrombosis and Hemostasis, 22 (2), pp. 197–202. (1996). Abstract only.

Zoldhelyi et al. Measurement of thrombin in virto, ex vivo, and in vivo by lectin affinity chromatography of the thrombin hirudin complex. Circulation 86 (4), supp. 1, p. I414. (Nov. 1992).

*Primary Examiner*—Ralph Gitomer
*Assistant Examiner*—Marjorie A. Moran
*Attorney, Agent, or Firm*—Burns, Doane, Swecker & Mathis, L.L.P.

[57] ABSTRACT

This invention relates to the use of an inhibitor of an activatable metabolic enzyme, which inhibitor is bound to a high molecular weight carrier, as a molecular marker for determining the activation of this enzyme for the diagnosis of the enzyme. The invention relates in particular to the use of a thrombin inhibitor, which is bound to a high molecular weight carrier, as a molecular marker for determining clotting activation in clotting diagnosis and therapy monitoring. The invention preferably relates to the use of dextran-hirudin or PEG-coupled hirudin as a molecular marker for clotting diagnosis and therapy monitoring.

14 Claims, No Drawings

COMPLEX-BOUND INHIBITORS OF METABOLIC ENZYMES CAPABLE OF BEING ACTIVATED, USEFUL AS MOLECULAR MARKERS FOR DIAGNOSTIC AND THERAPY MONITORING PURPOSES

The invention relates to the use of inhibitors of activatable or activated metabolic enzymes, which inhibitors are bound to high molecular weight carriers, as molecular markers for determining the activation of the enzyme in order to indirectly diagnostically and therapeutically monitor the enzyme.

This invention in particular relates to the use of an inhibitor of an activation product of the blood clotting cascade or of an activated fibrinolysis enzyme, which inhibitor is bound to a high molecular weight carrier, as a molecular marker to indirectly monitor an activation product of the blood clotting cascade or an activated fibrinolysis enzyme. The invention preferably relates to the use of a thrombin inhibitor, which is bound to a high molecular weight carrier, as a molecular marker for determining clotting activation in clotting diagnosis and therapy monitoring. The invention relates in particular to complex-bound hirudin (CBH) as a molecular marker for determining clotting activation.

Many metabolic physiological processes are regulated via cascade mechanisms, which are often branched, and in which an initiator or a chain reaction is intensified via a series of activatable enzymes. For example, mechanisms such as these are effective in the regulation of glycogen metabolism, in the transmission of extracellular signals and in blood clotting in particular. On a molecular level, sequential phosphorylation of the factors involved in a cascade mechanism is often to be found here. The intensification of an initiator by this mechanism is due to the enzymes which participate in the different stages of the mechanism being capable of modifying a plurality of substrate molecules, which themselves are often enzymes also. The activated enzymes of a mechanism such as this are suitable as molecular markers for determining the activation reaction which is proceeding in the body in each case. In a procedure such as this, specific, high-affinity inhibitors of the respective activated key enzyme are used which are to be fed as such to a permanent diagnosis line. This so-called molecular marker principle has only been developed unsatisfactorily hitherto, however.

The search for suitable molecular markers for the determination of intravasal activation reactions of blood clotting has been intensively pursued for some years. In the course of this work a series of metabolic products of clotting activation has emerged as molecular markers. These comprise prothrombin F1+2 fragments, platelet factor IV and fibrinopeptides A and B, as well as some cleavage products of fibrin decomposition (e.g. d-dimers) which are produced by fibrinolysis, and also comprise complexes formed between natural antithrombins and the serine protease thrombin, which are known as TAT complexes.

The usability of these molecular markers has been analysed in large-scale clinical studies. It has generally been ascertained that it is possible to determine blood levels of molecular markers of this type which are definitely increased or which persist during thrombotic occurrences or thrombo-embolytic diseases. The efficiency of these markers leaves very much to be desired, however. In clinical patients who suffered from venous thromboses or from arterial thrombotic occlusion diseases, the response capacity of the most sensitive marker for clotting, namely prothrombin fragment F1+2, was less than 20%. Moreover, no correlation could be found between the severity of the thrombo-embolytic disease or thrombotic occurrence and the magnitude of the blood level of this and other molecular markers.

From experience with persons suffering from diseases of this type, it can be deduced that in haemostaseology there has hitherto not been a principle of molecular measurement which enables conclusions to be drawn on the intensity of clotting activation by determining the actual blood level of the marker. The cause of this is that the molecular markers, as metabolic products of clotting enzymes which occur naturally in the body, are removed more or less rapidly from the circulation by elimination mechanisms. In this respect, it has to be taken into consideration that the markers are metabolised more or less rapidly, depending on the function of the organ concerned, particularly in the area of liver metabolism.

The underlying object of the present invention is thus to identify sensitive markers for the detection of an early phase of metabolic activation.

More particularly, an underlying object of the present invention is thus to identify sensitive markers for the detection of an early phase of clotting activation.

Moreover, the molecular marker should have a wide diagnostic range for the determination of intravasal activation reactions and more specifically for determining blood clotting reactions. In this respect, the marker should act in the organism independently of metabolic processes or elimination reactions. It must be ensured that the marker is distributed rapidly, exclusively in the blood circulation, is not metabolised or is only metabolised to a slight extent, and is only eliminated slowly.

This object is achieved by the use of a specific inhibitor of an enzyme involved in metabolism, which inhibitor is bound to a high molecular weight carrier, and thereby functions as an indirect marker for monitoring the activation or activity of this enzyme, e.g., an enzyme involved in the blood clotting cascade or fibrinolysis.

Surprisingly, it has now been found that inhibitors of an activatable metabolic enzyme, which inhibitors are bound to a high molecular weight carrier, i.e. complex-bound inhibitors of an activation product of the blood clotting cascade or of an activated fibrinolysis enzyme, are exclusively and rapidly distributed in the blood circulation, are only decomposed or eliminated slowly in the organism, and still have almost the same affinity for the enzyme as do the free, un-bound inhibitors. This principle can be employed for all activatable key enzymes for which high-affinity and specific inhibitors are available. It is particularly suitable for the activation products of the clotting cascade, such as thrombin, activated factor VII or activated factor X, and is also suitable for activated fibrinolysis enzymes, e.g. tissue plasminogen activator (tPA) or plasmin. Examples of other key enzymes involved in metabolism which can be inhibited by high-affinity specific inhibitors include angiotensin-converting enzyme (involved in blood pressure regulation) and elastase (involved in shock reactions).

The description given below relates to a preferred embodiment of the invention, namely the use of thrombin inhibitors. However, it should be understood that the molecular marker principle which is illustrated in this example for the diagnostic monitoring of blood can be employed correspondingly for any combination of an activatable enzyme and a high-affinity, specific inhibitor, which is bound to a high molecular weight carrier substance.

It has surprisingly been found that thrombin inhibitors which are bound to high molecular weight carriers (complex-bound thrombin inhibitors) are exclusively and rapidly distributed in the blood circulation, are only decomposed or eliminated slowly in the organism, and also always have the same affinity for thrombin as do free thrombin inhibitors and are thereby suitable for diagnostic purposes. It is not possible to use un-bound thrombin inhibitors for diagnoses of this type, because these substances are distributed in the body as a whole, not only in the blood, and when consumed they become redistributed without a detectable decrease in their concentration in the blood.

High-affinity natural thrombin inhibitors. e.g. hirudin, and also all other direct-binding synthetic thrombin inhibitors which have a high affinity for thrombin, can be used as thrombin inhibitors. Examples thereof include PEG-bonded 4-amidinophenylalanine (see Peptide Research 8, No. 2, 78–85 (1995)). Natural or synthetic substances can be used as the high molecular weight carriers. Examples include polyethylene glycol, dextran, and also blood proteins which occur naturally in the body. Other examples thereof include albumin, γ-globulins, and also ferritin, succinylated gelatine, crosslinked polypeptides, and polyhydroxy-starch.

A dextran-bound (DP) hirudin is suitable for use, as is hirudin which is coupled to polyethylene glycol (PEG), or hirudin which has been bound to human body proteins. Due to their molecular size, these proteins (albumin-bound hirudin or hirudins which are bound to defined gamma-globulins) only undergo a very slow biological elimination process.

Complex-bound hirudins of this type have the considerable advantage that they are distributed almost exclusively in the blood and exhibit no extravasation into the extracellular fluid space. Even small amounts of this marker, when distributed in the blood, can thereby function as a high-activity inhibitor, which binds rapidly and strongly, for intravasally activated thrombin or activated intermediates of the prothrombin-thrombin transformation. Due to the binding of the activated enzyme to the complex-bound thrombin inhibitor, the amount of "free" complexed hirudin is reduced by the extent to which active thrombin becomes available in the circulation.

Hirudin, and also hirudin which is bound to macromolecules, has high affinity for the serine protease thrombin. Its singular specificity exclusively for thrombin species allows this marker only to become active for this serine protease in the organism. Binding to other enzymes is not possible and is not known.

If the key enzyme of the clotting system, namely the serine protease thrombin, becomes available in the blood in the organism due to a permanent clotting activation, as the final product of intrinsic or extrinsic clotting, it is immediately bound and deactivated by the CBH molecular marker which is present in the blood. The amount of complex-bound hirudin, namely of the free inhibitor, decreases in flowing blood by the extent to which thrombin-hirudin complexes are formed.

The "free" molecular marker, namely complex-bound hirudin, is determined with the aid of a sensitive, specific method of detection for free hirudin which can rapidly be carried out. With the aid of this method of detection, discrete clotting activation effects can also be detected and quantified at an earlier point in time in the organism by repeated monitoring.

The molecular markers according to the invention are employed at a dose of 0.005–0.5 mg/kg, preferably 0.01–0.05 mg/kg, most preferably 0.01–0.02 mg/kg, with respect to the body weight of the patient. They are administered parenterally, preferably intravenously. Oral application, in which resorption of the marker is ensured by a corresponding formulation, is also possible. For this purpose, the molecular markers according to the invention are employed, together with customary adjuvant substances and carrier substances, in a formulation which is suitable for this method of administration. Thus, for example, complex-bound hirudin preparations can be produced either in a freeze-dried formulation (to be dissolved in 5 ml water; PEG-hirudin, albumin-hirudin, γ-globulin-hirudin) or as a ready-to-use injection solution (e.g. 5 ml; gelatine-hirudin, hydroxy-starch-hirudin), wherein the content of hirudin is appropriately 5 mg hirudin/ampoule. The requisite dose for the application is calculated according to the formula kg body weight: $20\hat{=}$ ml application volume and is administered as an intravenous bolus.

BRIEF DESCRIPTION OF THE FIGURES

FIG. 1 shows the effect of continuous thrombin infusion on the plasma level of PEG-hirudin/144 (140 U/kg).

FIG. 2 shows the effect of brief and repeated thrombin infusions (3×20 minutes) on the plasma level of PEG-hirudin /153 (150 U/kg).

FIG. 3 shows the effect of thrombokinase infusion on the blood level of dextran-hirudin.

The invention is explained in more detail with reference to the following example.

Example: Complex-bound Hirudin as a Molecular Marker

Patients from the group at risk were given an intravenously administered dose of complex-bound hirudin corresponding to their body weight. After a short distribution period (10–15 minutes) a constant blood level of this CBH was reached. The elimination half-life for CBH was known as a comparison quantity from corresponding control investigations on healthy test volunteers.

Small amounts of citrate whole blood (0.5 ml) were taken at short time intervals from patients at risk from thrombosis. The free circulating CBH was determined with the aid of a specific detection method for hirudin, namely the ecarin clotting time (ECT, European Patent No. 93 903 232.2). The ecarin clotting time is a method of determining activity and is extremely sensitive for the detection of free hirudin, but not for hirudin-thrombin complexes. There was a direct correlation between the decrease in the blood level of CBH and the intensity of thrombin liberation in the blood circulation. A quantification of the liberation of thrombin in the bloodstream with time was obtained due to the possibility of mathematically modelling the "rate of disappearance" or the more pronounced decrease in the blood level of free CBH. By using this method, it is even possible to detect early phases of clotting activation, which could not hitherto be achieved diagnostically.

In further tests, these molecular thrombin "probes" were checked for their efficiency in a modelling study applied to experiments on animals.

The experimental animals used here were rats (HAN-WISt, Central Experimental Animal Unit of the University of Jena) and rabbits (Chinchilla bastards, Savo, Bad Kislegg). Both male and female animals, conforming to the SPF livestock standard, were used from both species. The rats were narcotised with ethylurethane (1.5 g/kg subcutaneously), and the rabbits were narcotised with pentobarbital (25 mg/kg intravenously). Two different methods of detection were used as methods of determining hirudins in blood. In addition to the ecarin clotting time, a chromogenic substrate method was also used. In this method, chromogenic substrate (Chromozym TM, Pentapharm Basle) and ecarin (25 Eu/ml) or thrombin (1.5 NIH U/ml) were added to the plasma (diluted 1:10), and the extinction was measured in a spectrophotometer after two minutes (NIH U: International Standard for Thrombin Clotting Activity; NIH=National Institute of Health).

The complex-bound hirudin was used in two different hirudin preparations:

1. Dextran-hirudin (Dextran 150 kDa) was bound to hirudin by means of a method according to Walsmann et al. The specific activity was 971 ATU/mg (ATU=anti-thrombin units=International Standard for Direct Thrombin Inhibitors).

2. PEG-coupled hirudin. Commercial preparations supplied by Knoll were used (PEG-hirudin/144 or PEG/153).

1. Effect of Thrombin on the Plasma Level of PEG Hirudin in Rats

Experimental Design:

Narcotised rats were given PEG-hirudin in a dosage of 140 ATU/kg body weight, administered intravenously as a bolus (ATU=anti-thrombin units). 10 minutes later the rats were given an infusion of thrombin and the control animals were given the same infusion volume of saline. 0.5 ml of citrate blood was taken from the rats at 60 minute intervals via a permanent catheter in the jugular vein, so as thereby to monitor the blood level of the molecular marker. Thrombin was infused into the rats in the following concentrations over 360 minutes: 35, 70, 140, 250 and 500 NIH U/kg× hour$^{-1}$. The results are illustrated in FIG. 1. It can be seen that after a short initial distribution period a relatively constant blood level of PEG-hirudin was detected in the plasma. The approximate half-lives were about 12–14 hours. For an infusion of 35 NIH U/kg×hour$^{-1}$ thrombin, the time-dependence of the blood level of PEG-hirudin was almost identical to that of the control group (saline infusion). At 70 NIH U/kg×hour$^{-1}$ thrombin, a significantly accelerated decrease in the blood level of PEG-hirudin was detected even after 120 minutes. At higher doses of thrombin, free PEG-hirudin disappeared very rapidly from the blood circulation. At 250 or 500 NIH U thrombin, PEG-hirudin could no longer be detected in the plasma even after 120 minutes.

2. Effect of Repeated Thrombin Application on the PEG-hirudin Level of Rats

The PEG-hirudin (PEG153) which was used in these tests exhibited a time-dependence of its distribution and blood level which was almost the same as that in the test example described above. After a brief 15 minute infusion of 100 NIH U/kg thrombin in each case, only a discrete influencing of the PEG-hirudin level was detected after 120, 180 and 240 minutes, whereas on the application of 250 NIH-U/kg thrombin a more pronounced decrease in the PEG-hirudin blood level occurred after 3 hours; on increasing the dose to 500 NIH U/kg thrombin, this decrease was even greater.

3. Effect of Thrombokinase on the Plasma Level of Dextran-hirudin in Rabbits

The rabbits were pre-treated with 5000 ATU/kg of dextran-hirudin. From the monitoring of the dextran-hirudin blood level it could be seen that a constant hirudin blood level in the rabbits first detected after 24 hours. On the infusion of a purified thrombokinase solution (1 ml/kg/hour) over 6 hours, a more pronounced decrease in the dextran-hirudin blood level was detected. For these investigations, the results of five separate tests were combined.

It follows from these investigations that dextran-hirudin has a very long distribution phase (24 hours) in rabbits, due to the interactions of the dextran with surface structures of the endothelium cells, with the RES of the liver and with the corpuscular constituents of the blood. For this species of animal, dextran-hirudin was only of limited suitability for marker investigations. It could not be identified from these investigations whether the dextran-hirudin was also distributed in deeper compartments of the rabbit organism. In contrast, the PEG-coupled hirudins (PEG 144 and 153) proved to be suitable for corresponding molecular marker modelling in the tests on rats which are presented here. A relatively constant distribution equilibrium was attained in the circulation of rats, even after 10 minutes, and modelling of intravasal clotting activation by means of the continuous infusion of small amounts of thrombin, or by the discontinuous application of thrombin, could be followed and measured by a corresponding disturbance of the PEG-hirudin blood level.

It can be deduced from these modelling investigations of animal experiments that complex-bound hirudins are suitable as molecular markers for intravasal clotting activation. The advantage of the molecular markers which are presented here is that high molecular weight hirudin complexes of this type are not subject to any elimination function in the organism. They are permanently available for binding active thrombin, which can occur permanently in the circulation as a final activation product of clotting activation. A definite clotting activation can be quantified by a sensitive method of detecting the level of free marker.

We claim:

1. An method for indirectly quantitating a known enzyme, comprising the following steps:
   (1) parenterally administering to a subject in need of such monitoring an amount of an inhibitor-high molecular weight complex or inhibitor-high molecular weight conjugate, which inhibitor-high molecular weight complex or conjugate specifically binds to said enzyme to produce a complex;
   (2) measuring the change in the circulating amount of said inhibitor-high molecular weight conjugate or complex in the blood of said subject after administration; and
   (3) correlating said change to the amount of said enzyme.

2. The method of claim 1, wherein the enzyme is one known to be involved in one of (i) a reaction in the clotting cascade, (ii) fibrinolysis, (iii) a metabolic physiological process, and (iv) shock.

3. The method of claim 1, wherein said enzyme is selected from the group consisting of thrombin, factor VII, factor X, tissue plasminogen activator (tPA), plasmin, angiotensin-converting enzyme and elastase.

4. The method of claim 1, wherein the inhibitor is a thrombin inhibitor.

5. The method of claim 4 wherein said thrombin inhibitor is hirudin and the enzyme which is indirectly determined is thrombin.

6. The method of claim 1, which is used to indirectly measure thrombin in order to monitor clotting function.

7. The method of claim 8 wherein said inhibitor is hirudin.

8. The method of claim 1, wherein the high molecular weight compound is selected from the group consisting of dextran, polyethylene glycol (PEG), albumin, gamma-globulin, ferritin, succinylated gelatin and polyhydroxystarch.

9. The method of claim 1, wherein the enzyme which is indirectly monitored is one that catalyzes a fibrinolytic reaction.

10. The method of claim 1, wherein the enzyme which is indirectly monitored is one that catalyzes a reaction in the clotting cascade.

11. The method of claim 1, wherein the inhibitor-high molecular weight compound conjugate or complex is dextran-hirudin or PEG-hirudin.

12. The method of claim 1, wherein the amount of said inhibitor-complex or conjugate administered to said subject ranges from 0.005 to 0.5 milligrams per kilogram.

13. The method of claim 12 wherein said amount ranges from 0.01 to 0.05 milligrams per kilogram.

14. The method of claim 13 wherein said amount ranges from 0.01 to 0.02 milligrams per kilogram.

* * * * *